US011263230B2

(12) United States Patent
Chan et al.

(10) Patent No.: US 11,263,230 B2
(45) Date of Patent: Mar. 1, 2022

(54) METHOD AND SYSTEM OF INTELLIGENT NUMERIC CATEGORIZATION OF NOISY DATA

(71) Applicant: KONINKLIJKE PHILIPS N.V., Eindhoven (NL)

(72) Inventors: Tak Ming Chan, Shanghai (CN); Choo Chiap Chiau, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/134,270

(22) Filed: Sep. 18, 2018

(65) Prior Publication Data
US 2019/0102443 A1 Apr. 4, 2019

(30) Foreign Application Priority Data

Sep. 29, 2017 (WO) ................. PCT/CN2017/104289
Oct. 27, 2017 (EP) ..................................... 17198804

(51) Int. Cl.
*G06F 3/0484* (2013.01)
*G06F 16/26* (2019.01)
*G06N 7/00* (2006.01)
*G06K 9/62* (2022.01)
*G16H 50/00* (2018.01)

(52) U.S. Cl.
CPC ............ *G06F 16/26* (2019.01); *G06F 3/0484* (2013.01); *G06K 9/623* (2013.01); *G06K 9/6212* (2013.01); *G06K 9/6218* (2013.01); *G06N 7/005* (2013.01); *G16H 50/00* (2018.01); *G06K 9/6219* (2013.01); *G06K 9/6282* (2013.01)

(58) Field of Classification Search
CPC . G06F 17/30572; G06F 3/0484; G06N 7/005; G06K 9/623; G06K 9/6218
See application file for complete search history.

(56) References Cited

U.S. PATENT DOCUMENTS

| 6,604,115 | B1 | 8/2003 | Gary, Jr. et al. |
| 2002/0165845 | A1* | 11/2002 | Gogolak ................. G16C 20/30 |
| 2003/0176931 | A1 | 9/2003 | Pednault et al. |

(Continued)

FOREIGN PATENT DOCUMENTS

| WO | 2007147166 A2 | 12/2007 |
| WO | 2016030436 A1 | 3/2016 |

(Continued)

OTHER PUBLICATIONS

Schirdewan, et al., "Cardiac magnetic field map topology quantified by Kullback-Liebler entropy identifies patients with hypertrophic cardiomyopathy", 2007 American Institute of Physics, CHAOS, vol. 17, No. 1, Mar. 30, 2007, pp. 015118-1-015118-10.

(Continued)

*Primary Examiner* — Anil K Bhargava
(74) *Attorney, Agent, or Firm* — Micah-Shalom Kesselman (57) ABSTRACT

A data processing system and related method. The system comprises an input interface for receiving data to be datamined for a target. A categorizer configured to compute one or more category operators suitable to categorize said data. The computing by the categorizer of the category operators includes computing a metric. The system further includes an output interface for outputting the so computed one or more category operators.

9 Claims, 5 Drawing Sheets

(56) References Cited

U.S. PATENT DOCUMENTS

| | | | | |
|---|---|---|---|---|
| 2004/0002929 | A1* | 1/2004 | Kim | G06F 17/18 706/21 |
| 2004/0243362 | A1* | 12/2004 | Liebman | G16B 25/10 703/2 |
| 2010/0088264 | A1* | 4/2010 | Teverovskiy | G16H 50/20 706/46 |
| 2012/0033863 | A1 | 2/2012 | Wojton et al. | |
| 2014/0278115 | A1* | 9/2014 | Bas | G01V 99/005 702/14 |
| 2015/0026606 | A1* | 1/2015 | Hill | G06F 3/0482 715/760 |
| 2016/0232160 | A1* | 8/2016 | Buhrmann | G06F 16/248 |
| 2016/0232457 | A1* | 8/2016 | Gray | G06T 11/206 |
| 2016/0358040 | A1* | 12/2016 | Fang | G06N 7/02 |
| 2017/0053064 | A1* | 2/2017 | Bhavani | G16H 40/63 |
| 2019/0387996 | A1* | 12/2019 | Du | A61B 5/0022 |

FOREIGN PATENT DOCUMENTS

| | | |
|---|---|---|
| WO | 2017072010 A1 | 5/2017 |
| WO | 2017-10-05 A1 | 10/2017 |

OTHER PUBLICATIONS

EP Search Report for related Application No. EP17198804.
"SAS:Analytics, Arifical Intelligence and Data Management", SAS India, News Blog, Originally Downloaded in Jun. 2016 From http://www.sas.com/en_in/home.html.
IBM, SPSS Software Blog, Originally Downloaded From http://www-01.IBM.com/software/analytics/spss, Jun. 2016.
Wikipedia, "Information Gain in Decision Trees"; Originally Downloaded From: http://en.wikipedia.org/wiki/information_gain_in_decision_trees, Jun. 2016.

* cited by examiner

METHOD AND SYSTEM OF INTELLIGENT NUMERIC CATEGORIZATION OF NOISY DATA

CROSS-REFERENCE TO RELATED APPLICATIONS

This application claims the benefit of EP Application No. 17198804.1, filed on Oct. 27, 2017 and of PCT/CN2017/104289, filed on Sep. 29, 2017. These applications are hereby incorporated by reference in their entirety.

FIELD OF THE INVENTION

The invention relates to data processing systems, data processing methods, a data arrangement, to a computer program element and to a computer readable medium.

BACKGROUND OF THE INVENTION

The healthcare industry uses management systems such as Cardiovascular Information Systems (CVIS) or Clinical Data Repositories (CDR).

Such data management systems may record large number of attributes (or properties) for patients in a specialized area, such as cardiology or other.

The data in such data management systems may be analyzed by data analytics tool to find patterns, for modeling and predictive analytics.

Visual analytics and pattern discovery tools for such data are known from Applicant's WO2016/030436A1, WO2017/072010A1 and WO2017/072628A1 for advanced data analytics in a visual and interactive way for domain users. Searching for patterns in data is an instance of data-mining.

Pattern discovery tools may be used for interpretable predictive modeling for minority (and even rare) targets, with rates as low 2% (or even less) of the total data. Mining for such rare targets may be useful in real-world applications: examples for rare but useful targets in the medical field include adverse cardiac events, cases of unmet key performance indicators (KPI), and malfunctioned imaging machines in healthcare.

Finding interpretable prediction models for targets, in particular for rare ones, from historical real-world data is valuable yet challenging. One example in cardiology with real use-cases is finding patterns of dead outcomes, after patients go through a procedure called percutaneous coronary intervention (PCI) to treat narrowed heart vessels. A pattern of dead outcomes, discovered in a data-driven manner with statistically significant predictive power, can provide new (sometimes surprising) insights beyond the conventional domain experience for advanced clinical research and potential clinical studies.

To handle mixed numeric and categorical data, existing prediction methods either sacrifice interpretability by treating all attributes as numbers, or sacrifice potentially valuable information by utilizing only categorical attributes. In the former case treating all attributes as numbers, examples like linear or logistic regression, will estimate certain coefficients (weights) for the numeric attributes in their prediction model learned (trained) from labelled historical data.

Existing pattern discovery system works only with categorical data attributes in order to generate interpretable patterns. For numeric data attributes, it relies on a configuration module with transformation rules that categorize them with domain knowledge. For example, body mass index (BMI) can be categorized as normal or abnormal according to a localized clinical guideline. In real-world applications, however, a numeric attribute does not necessarily have a known guideline for categorization, and a generic guideline may not capture the data specific properties. For example, lengths of stents to treat narrowed heart blood vessels do not have any guidelines, but this information may still useful to predict adverse clinical outcomes in cardiology.

SUMMARY OF THE INVENTION

There may therefore be a need for an improved handling of data.

The object of the present invention is solved by the subject matter of the independent claims where further embodiments are incorporated in the dependent claims. It should be noted that the following described aspect ("first aspect") of the invention equally applies to the data processing methods, to the computer program element and to the computer readable medium.

According to a first aspect of the invention there is provided a data processing system, comprising:

an input interface for receiving data to be data-mined for a pattern given a target;

a categorizer configured to compute one or more category operators suitable to categorize said data, wherein the computing by the categorizer of the category operators includes computing a metric; and an output interface for outputting the so computed one or more category operators.

The term "category operators" as used herein, refers to an expression that allows given attributes in the data to be categorized. For instance, category operators include thresholds, single ranges and multiple ranges definable by numbers. A threshold is defined by a single number as its bound. In case of range(s)) one or more pairs of numbers are required that define the respective upper and lower bound. The manner of comparison (eg, "<"versus" >=", etc) as expressed by the category operator defines its type.

The metric is function of parameters of the category operators. The parameters include the type and/or one more numeric variables that define bound(s) for the category operators to be computed. To allow for improved results, the metric is furthermore a function of the target itself as envisaged herein in a preferred embodiment.

According to one embodiment, the system comprises a data-mining component configured to mine, or help a user to mine, the data categorized by the one or more category operators, for a pattern.

It has been found that with some data mining tools, some categorizations yield better results than others. Data mining is the process of finding patterns, that is, relations between attributes of the data and a target. A target is one or more quantities of interest.

According to one embodiment, the metric includes any one of i) an entropy based quantity, in particular information gain or Kullback-Leibler divergence, ii) a misclassification error, iii) Gini index. Specifically and preferably, the categorizer is configured to compute the operators by optimizing for the metric, the metric being suitably chosen to represent a desirable property, such as information growth (in the information theoretic sense) or other quantity that allows defining a desirable property of the categorization one wishes to compute.

According to one embodiment, the categorizer can be implemented as an information gain maximization algorithm (or a misclassification error minimization, or a Kullback-Leibler divergence) based on the category operators.

The data categorized by the computed category operators are processed by a data mining component. The data mining component runs a suitable pattern discovery algorithm to discover the underlying pattern. The pattern may be constituted by a model, such as a constructed decision tree in a decision tree learning algorithm, or other. Alternatively, the data mining component is interactive in that it helps a user to discover the pattern. This is the case in particular for so called "interpretable", more graphics driven data mining tools. For such data mining tools, a "pattern" for present purposes may also include a graphic representation, suitably color- or shape-coded to represent the relationships between the target and the categorized attributes, the categorization being based on the category operators computed by the categorizer. Interpretable data mining algorithms envisaged include rule generation, logistic regression, and others, based on the category operators.

According to one embodiment, said data includes at least one record with at least one missing value, with the categorizer configured to ignore said at least one record when computing at least one of the one or more category operators.

A robustness in relation to noise in the data can be achieved by ignoring records with at least one missing value as mentioned above. In particular, when executing an algorithm to compute the COs, a missing value for the relevant attribute is skipped and the computation is solely based on non-missing values from other records. This prevents information loss introduced via removing missing records or attributes. The categorizer checks each attribute for missing values and, if missing values are found, it computes the category operators only on the non-missing values. In particular, the proposed categorizer as proposed herein, does not attempt to fill the missing value by inter- or extrapolation from other records. Specifically, no replacement value for the missing value is input in the algorithm for computing the category operator. This is because "filling" of missing values for attributes in this manner has been observed at times to appreciably distort the results of the category operator computations. A record may be ignored for missing values for a certain attribute, but may then be still included later, in relation to another attribute, if a value is present in that record for the other attribute. Preferably the check for missing values is performed "on-the-fly" in between the computation of the respective category operators for different attributes. In other words, the missing value check operations and the category operator computations are interleaved. This can be implemented in a nested looping scheme. This allows presenting results quickly, even for a large data set, rather than doing the checks on the entire data set upfront before computing the category operators. In particular, with the proposed system, no data cleansing is required to before the categorization can commence.

According to one embodiment, the system includes a user interface that allows a user to change any one or a combination of i) the data, ii) the one or more computed category operators, and, in response to said change, i) the categorizer configured to rec-compute the one or more category operators and/or ii) the or a data-mining component configured to re-mine the data. Preferably the user interface is a graphical user interface that is rendered for display on a display unit. In other words, although the categorizer is preferably envisaged herein to perform the computation of the category operators automatically, the user can still use the interface to tweak the results to incorporate domain knowledge for instance.

According to one embodiment, the graphics display generator is configured to render on a display unit a graphics display that includes a representation of the pattern and/or of the categorized data.

According to one embodiment, the categorizer configured to compute a plurality of said category operators and configured to rank same according to said metric.

According to one embodiment, the or a graphics display generator is configured to effect display of some or all of the so ranked category operators.

According to one embodiment, the system comprises a conversion component configured to reduce a plurality of string values in the data into numeric values according to their frequency and/or similarity, before the categorizer CAT computes the category operators. In other words, a dimensional reduction is achieved to speed up the computation of the category operators.

According to a second aspect of the invention there is provided a data processing system, comprising:
a categorizer configured to compute one or more category operators suitable to categorize data to be data-mined for a pattern and/or a data-mining component configured to mine the data for a or then pattern, and
a user interface configured to allow a user to change any or a combination of i) the data, ii) the computed category operators, and, in response to said change, the categorizer configured to rec-compute the one or more category operators and/or the or a data-mining component configured to re-mine the data.

According to a third aspect of the invention there is provided a method of data processing, comprising the steps of:
receiving data to be data-mined for a target;
computing one or more category operators suitable to categorize said data, wherein the computing of the category operators includes computing a category metric; and
outputting the so computed one or more category operators.

According to one embodiment, the method includes:
providing a user interface and receiving therethrough a request by a user to change any one or a combination of i) the data, ii) the one or more computed category operators, and,
in response to said change, rec-computing the one or more category operators and/or ii) the or a data-mining component configured to re-mine the data. Preferably the user interface is a graphical user interface that is rendered for display on a display unit.

Preferably, the user interface is a graphical user interface and is provided by having it displayed on a display device.

According to one embodiment, the method comprises rendering on a display unit a graphics display that includes a representation of the pattern and/or of the categorized data. The displaying of the pattern and/or of the categorized data may be done in combination with displaying the graphical user interface.

According to one embodiment, the method comprises computing a plurality of said category operators and ranking same according to said metric.

According to one embodiment, the method comprises effecting display of some or of all the so ranked category operators.

According to one embodiment, the method comprises reducing a plurality of string values in the data into numeric values according to their frequency and/or similarity, before computing the category operators.

According to a fourth aspect of the invention there is provided a method of data processing, comprising the steps of:

computing one or more category operators suitable to categorize data to be data-mined for a pattern and/or data-mining the data for a pattern, and generating a user interface configured to allow a user to change any or a combination of i) the data, ii) the computed category operators; and in response to said change, rec-computing the one or more category operators and/or re-mining the data.

According to a fifth aspect of the invention there is provided an arrangement comprising: a system of any one of previously mentioned aspects or embodiments and a data memory holding said data.

According to a sixth aspect of the invention there is provided a computer program element, which, when being executed by at least one processing unit, is adapted to cause the processing unit to perform the method as per any of the aspects or embodiments mentioned above.

According to a seventh aspect of the invention there is provided a computer readable medium having stored thereon the program element.

BRIEF DESCRIPTION OF THE DRAWINGS

Exemplary embodiments of the invention will now be described with reference to the following drawings, which are not to scale, wherein.

DETAILED DESCRIPTION OF EMBODIMENTS

Figure 1:
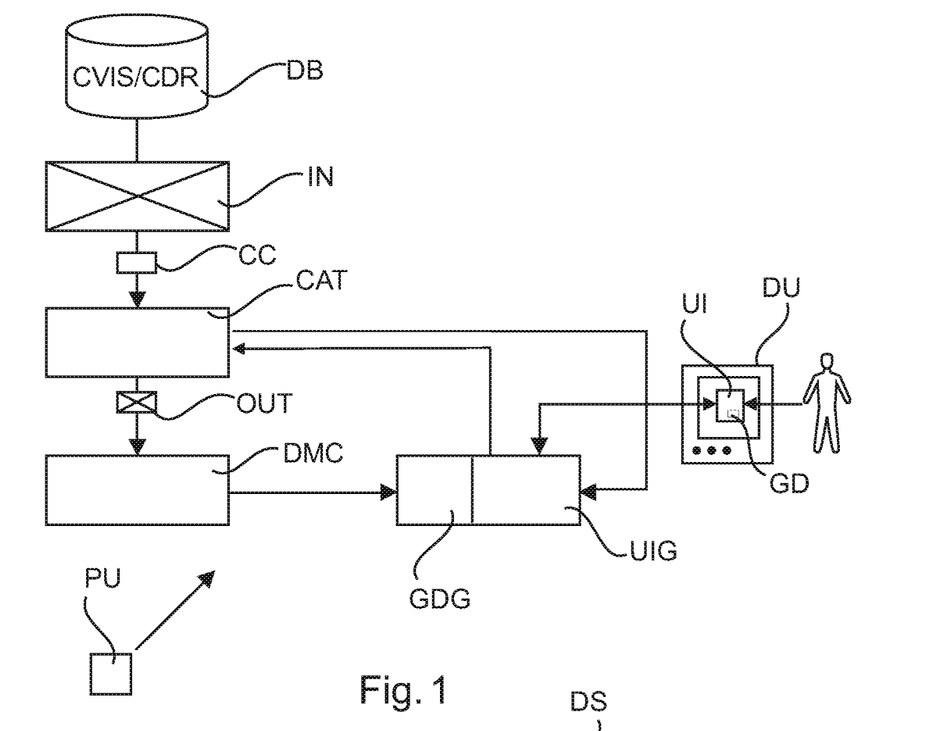
FIG. 1 shows a block diagram of a data processing system.

With reference to FIG. 1 there is shown a schematic block diagram of a computerized arrangement 100 for processing data held in a data base DB or other memory. More specifically and very broadly the arrangement comprises one or more processing units PU that provide functionalities that allow some or all of the data in the data base DB to be categorized and optionally to process the categorized data for data mining purposes, to so discover certain patterns of interest as (possibly latently) encoded in the data. Such patterns may include, for instance, deterministic or statistical relationships or rules, either explicit or implicit, clusterings, etc as will be explained in more detail.

The computerized arrangement 100 is mainly envisaged for processing medical data such as held in a clinical data repository CDR, e.g., in cardiovascular information systems CVIS. CVIS hold records of patients who underwent a cardiac intervention, in particular a percutaneous intervention (PCI) where a stent is placed in the patient's vessels to treat a stricture. We shall frequently revisit this particular example about CVIS data below although other medical applications are not excluded herein. For the avoidance of doubt, it is also non-medical fields of application, for instance control or management of a computer or communication network, management of other devices and machines (e.g., robots, vehicles, etc.) are also not excluded herein.

According to one embodiment, the computerized arrangement is configured as a predictive analytics system with intelligent auto-numeric categorization for the prediction of targets of interest on potentially noisy data as held in the data memory DB. In other words, the arrangement allows for "intelligent" numeric categorization of data in the sense that the categorization is performed automatically and yet it allows the user to interactively tweak or override the results to so still incorporate user's domain knowledge incorporation.

Figure 1A:
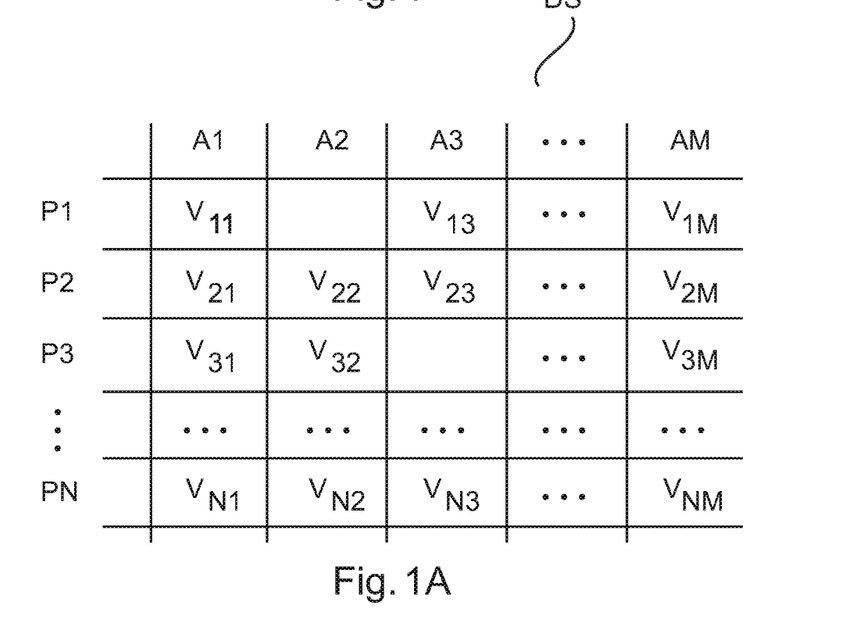
FIG. 1A shows a schematic representation of data processable by the system of FIG. 1.

Before describing further details of the data processing arrangement 100, reference is now made to inset FIG. 1A. FIG. 1A shows a schematic representation of a data set DS processable herein. Preferably, but not necessarily in all embodiments, the data is structured and arrangeable in rows and columns as shown in FIG. 1. An exemplary embodiment of this are patient records P1-PN with different attributes A1-AM. In the representation of FIG. 1A, "A1"-"AM" represent alphanumeric strings that each stand for a certain attribute that a patient $P_j$ may or may not have. Possible attributes of interest include for instance age, body mass index, the type of medical treatments experienced, medical methodology used and specifics on the medical devices used in the intervention, etc. Again, although main reference will be made herein through to medical applications and medical patient records, this is solely for the purpose to elucidate the principle of operation of the proposed arrangement 100 and is not to restrict to the present disclosure to medical applications. Some attributes across the records have a certain value $v_{ij}$. The values $v_{ij}$ are preferably numeric and provide a quantification of the associated attribute. For instance, a value $v_{ij}$ indicates a magnitude or quantity for attribute $A_j$ that applies to patient $P_i$. For instance, a given patient $P_i$ may have a body mass index ("BMI") of 25. The number 25 is hence the value of the attribute "BMI" for the said patient. Also as indicated in FIG. 1A, not all records or attributes may in fact have a value. In some instances, there may be records with missing values. This is indicated by example in the FIG. 1A by a blank entry for records P1, P3 at attributes A2, A3, respectively. In other words, some records may include one or more empty strings or any other string that indicates that no value has been recorded for that patient for the specific attribute. Some records may include values for some attributes but not for others. The reasons for having missing values may simply be that a certain measurement for the attribute has not been taken, or due to data capture failure, e.g. the data was mistakenly not entered into the data base. Missing data in the data records shown above constitutes an instance of data noise and the proposed data processing arrangement is configured to be noise tolerant and robust as will be explained in more detail below. It will be appreciated that the particular representation of the data set DS in rows and columns is not limiting. For instance, a transposed representation where rows and columns are exchanged are also envisaged and so are other representations such as cross-pointer structure that are not necessarily stored in row and column form as shown in FIG. 1 but can be transformed into such if required. What is envisaged, however, is a structuring of the data set DS by means of attributes. The data set DS is potentially high dimensional, as the number of patients can run into the 10s or 100s of thousands and the number of attributes may be in the 10s or 100s or even thousands.

The attributes can be categorized based on dichotomization (thresholding), or single or multiple (numerical) ranges or intervals. A categorization of the attributes induces a categorization of the underlying patient record. For instance, one may be interested in all those patients whose body mass index attribute is less than 25. This is an instance of dichotomization or thresholding against the threshold operator "less than 25". The term category operators as used herein, refers to an expression or device that allows given attributes to be categorized. In more detail and more formally, a category operator (CO) is a mapping CO: D-> $\{l1,l_2, \ldots lp\}$ from a domain (e.g., the set of all patients) to a discrete set of labels $\{l1,l_2, \ldots lp\}$, each label representing one of the categories. Each category operator is definable in terms of a numerical comparator such as:

$$<*,>=*,>*,<=,*[*,*],[*,*),(*,*],(*,*) \quad (1)$$

with a number being required at each placeholder "*". The expressions (1) define the type of the category operator. A CO is hence any one of:

$$<a,>=,>a,<=,a[a,b],[a,b),(a,b],(a,b), \text{ with } a,b<\infty \text{ any finite numbers} \quad (2)$$

In other words, (2) are interval definitions: one-sided (with a single numeric bound "a" or threshold) or two-sided with two numeric boundaries, a lower bound "a" and an upper one "b". Each specific comparator defines a type of the category operator. In other words, a category operator is completely defined by the following parameters: i) its type (1) and ii) by specific number(s) a or a, b to fill the placeholders "*". Once these parameters are specified, one arrives at the category operator as per any one of (2).

A categorization by a collection of multiple intervals such as $[a_1,b_1]$, $[a_2,b_2]$, ... etc. is also envisaged and so is any collection of operators CO of any type as per (2) in any combination. Each comparator can operate on an attribute. Each category has a "power" or "size" which is the total number of those domain elements (e.g., patients x) whose attribute satisfies the comparator: $CO^{-1}(l_j)=\{x \text{ in } D|CO(x)=\text{"true"}\}$, with "$^{-1}$" indicating the inverse image of category operator CO. For example, the size of the comparator "BMI>25" is the number of all those patients whose body mass index is less than 25, etc. It will be appreciated, that each category operator CO can be flipped into its logic complement. For instance, the complement of the operator "BMI<25" is "BMI>=25", that is a body-mass index larger or equal to 25 etc. If the operator CO is single range, the complement is all those values outside the range. For an operator CO formed from a collection of disjoint multiple ranges, the logical complement is the category operator that satisfies all those attribute values that do not lie in any of those multiple ranges etc. Each category operator as envisaged herein is associated with a respective one or more attributes it can operate on. The categorization operators completely define a categorization of the underlying domain. That is, for each patient record it can be decided, by applying the category operators against the relevant attribute, which category the patient/record falls under.

As envisaged herein, the data is categorizable once suitable category operators have been found. The data and the category operators for the attributes of interest may then form the basis of data mining or pattern discovery, both terms being used here interchangeably. Broadly, in pattern discovery or data mining as envisaged herein one asks for a relationship between variables as indicated above. Specifically, a user manually selects one or more target variables for interest. The question that may be asked then is: "what is the relationship between these target variables and the attributes in the data?" More specifically, one may be interested in what particular combination on configuration of the attribute values across the data set gives rise to the specific target selected. Yet more specifically and as an application to cardiovascular data collected for patients who underwent percutaneous stent deployment or similar, one may ask for the target to be the outcome of the intervention. This is binary target, the outcome being whether the patients as recorded in the set DS are alive or not at a given instant of time. Data mining the patient records for this target (OUTCOME="deceased" or "alive") might then reveal which attributes or combination thereof (age, body mass index, length of stent used etc.) is mostly determinative for whether or not the patient survives the intervention. One may then product for a new patient (whose record has not yet been processed) the outcome. This obviously will be of tremendous benefit for any health care system and the efficient management of resources.

The pattern to be discovered may be given in term of a model. The "model" may be explicit in terms of a formula between attributes and target or may be more implicit such as the collection of suitably adjusted weights of nodes of a neural network or the branches of a constructed decisions tree with interrogation at each leaf based on the computed category operators, etc. The model may also be statistical rather than deterministic. The model preferably allows predictions, so the model may be referred to herein as "predictive model". Specifically, given the model, predictions can then be made for "new data" not among the initial data set as to whether the new data, with given attributes, will or will not fulfill the target. For instance, eg one may be interested whether a given patient will or will not eventually survive the intervention given their history as encoded by the attributes in his or her record.

The data mining or pattern discovery may be implemented herein by any suitable data processing algorithm, in particular, but necessarily, machine learning algorithms such as decision trees, neuronal networks, support vector machines (SVM). Other algorithms are also envisaged herein, such as regression techniques, principal component analysis (PCA) and others.

In addition to the essentially fully automatic data mining algorithms mentioned above, there is another class of data mining tools envisaged that are not configured in and of itself to find a pattern but are configured to help a human user to find a pattern by interaction with the data. This type of interpretable data miner tools may hence be called "semi-automatic" due to the level of user involvement. The term "mining for data" is hence understood herein to cover both of these variants (and a combination of the two). This later type of data mining tools will be referred to herein as "interpretable" data miner tools. One such type of interpretable data mining tools allows a user to map, by a suitable graphics display generator, the categorized data to graphical elements which are then displayed on a screen. The graphical elements include geometrical elements, areas, shapes and have a color or hue. The relationships between the categories and their respective sizes may then be visually modulated by changing area size, color or hue of the graphical element to visually convey to the user underlying relationships. Examples of such data miner tools are those that map categories/COs on waterfall charts, pie-charts, histograms, or other visual aids. In addition or instead of rendering the categories graphically, descriptive statistics are computed and displayed instead or alongside the graphical aids, such as averages, standard deviations, number or false positives, random baseline, statistical significance (p-values), predictive power (f-measure), odds-ratio, etc. This may allow visually finding dominant factors to better understand a causality of target. A dominant factor for the manifestation of a target may present itself as a relatively large size of a certain category of a given target. For instance, it may turn out that a large proposition of those patients who did not survive had a high BMI. The BMI may hence turn out a dominant factor for the particular intervention and the BMI of any future patient may hence be taken well into account before deciding to go ahead with the intervention. As will be understood from the above, in particular for the interpretable type of data mining tools, a complete description of the predictive model may not necessarily be obtained. As suitable graphical representation of the categories relative to the target may be sufficient to visualize clusters or dominant factors of category. A category may be called "dominant", and its category operator suitably chosen, when for instance a relative large proportion of the underlying domain falls into said category whilst meeting the target.

Some of these algorithms, and in particularly the interpretable ones as mainly envisaged herein, can be used efficiently if the data is categorized in a meaningful manner, that is, in a manner that more lucidly lays bare a pattern.

The proposed arrangement 100 then allows to find automatically, and on a rational basis, a suitable categorization of the data. The categorized data can then be fed into suitable data mining algorithms as discussed above to search for a pattern between attributes and the target. More specifically, the proposed arrangement implements auto-numeric categorization of the data that is preferably directly informative for the prediction target and directly interpretable by the user as is the case for interpretable data mining tools. In addition, the proposed system 100 preferably allows a flexible interactive user categorization that allows domain knowledge incorporation for real world-applications. In short, the proposed data processing arrangement allows for intelligent numeric categorization for predictive analytics purposes.

In more detail, and referring now back to the block diagram of FIG. 1 the arrangement 100 includes an interface IN through which the structured data DS in the data base or memory DB can be accessed by the arrangement. A user defined selection or the entirety of the data is then categorized for all or a sub-selection of attributes. This sub-selection is usually done by the user. The categorization is performed, preferably automatically, by a categorizer component CAT. To this end, the categorizer CAT computes category operators for all or the sub-selected attributes. The categorizer then outputs the computed category operators through an output OUT. The output category operators are then used by a data mining component DMC to compute a pattern or to at least facilitate finding same by the user. Preferably the data mining component DMC is of the interpretable type as explained above, but other data mining algorithms, machine learning based or otherwise as discussed above are also envisaged. In other words, the categorizer can be used as a pre-processor for existing data miners, interpretable or not.

The earlier mentioned rational basis for finding the category operators may be established by a metric system supported by the categorizer CTA. It turns out that some categories are more suitable than others to derive patterns/dominant factors for the target when mining for them. It is hence proposed to choose a metric that captures this suitability.

In one embodiment, the metric allows defining a system to ensure that the computed category operators are optimal in a defined sense relative to that metric.

Computation of the category operators by categorizer CAT as envisaged herein in one embodiment requires that the user has to pre-specify in particular the type of the computed category operators for each attribute of interest. Alternatively, the types can be pre-set or are selected automatically.

Computing of the category operators according to the metric as proposed herein can be formulated in terms of a function of the threshold a or, if ranges are sought, of the upper and/or lower bounds a,b for the range type category operator. Specifically and in one embodiment, an optimality criterion is formulated as an objective function o( ), which is a function of the single bound or of one or more bound, $o(a)$ or $o(a_1, b_1, \ldots, bj, aj, \ldots)$ ($j \geq 1$). The objective function maps into the earlier mentioned metric. The metric is a number. The objective function may hence also be referred to herein as the scoring or cost function.

The CAT runs an optimization algorithm to optimize the objective function o( ) and to so find the bound a or bounds $a_j, b_j (j \geq 1)$ for the category operators that optimize the metric. Optimizing for the bounds to find the category operators is but one algorithmic embodiment and other variants are also envisaged herein. Any type of numerical optimization algorithms is envisaged, such as conjugate gradients, Newton Raphson. Alternatively, or in addition, search algorithms, such as of the greedy type, etc. may be used. Optimization may require either a minimization or a maximization. The optimization may not necessarily return a global optimum (minimum or maximum), but at one or more local optima may be sufficient. Also, the optimization may be aborted earlier before even reaching the local optimum once it is decided that sufficient convergence has been achieved. In one embodiment the information theoretic concept of information gain is used as the metric to find an optimal categorization. Specifically, the categorization may be implemented as an information gain maximization algorithm. More generally, other, in particular entropy based metrics, such as the Kullback-Leibler divergence may be used to define the metric to find the best category operators. Alternatively, a classification error minimization, is used. Further embodiments include maximization of informative/predictive metrics/measures such as Gini index or the reciprocal of misclassification rates. Preferably, the target is included as an input in the computation of the metric to derive target specific category operators.

The metric will be referred to hereinafter also as a "score" (or "cost"), depending on the nature of the optimization. In the following reference will be made mainly to "score" but all that is said is of equal application to when the metric is defined as a "cost". "Score" is used when the metric is to be maximized whilst the wording cost may be used if the metric is to be minimized.

The category operators computed for each attribute can be ranked according to their respectively best metric, eg score high or cost low, as computed in the optimization.

As will be explained in more detail in relation to the method flow chart, the categorizer is configured for enhanced robustness against noise in the data DS. This is achieved in one embodiment by having the optimization algorithm of the categorizer CAT ignore data sets with missing values at the respectively considered attributes. Specifically, the categorizer CAT is configured in one embodiment to not compute surrogate or replacement values of the missing values but to skip these records and to not include these as input when optimizing the score for a given attribute for which there are missing value(s).

Optionally, the data processing arrangement includes a conversion tool CC that allows reducing number of attributes to ease computation of the category operators. This may be called a dimension reduction. This is advantageous in particular for large patient data records that may include multiple ostensibly different attributes that, however, essentially relate to the same attribute. For instance, after consolidating data records from many data bases, the attribute that a patient has diabetes for instance may be indicated by different attribute identifier such as "DIABETES", "DIAB", "DIB", "DIM" or other variants thereof. Running the proposed categorizer and the data mining component on such a data with unnecessarily large number attributes, may require a lot of CPU time. The conversion tool CC therefore operates to consolidate the variants of the same attributes into a single one by converting the string values (that are not necessarily numeric) of the different attribute variants into respective numeric values. The conversion into numbers may be done according to frequency of records with a specific value, or string similarity as they occur in the data records DS. Huffman or distance based coding may be used for encoding the alpha numeric strings (which are not necessarily numbers) into numbers whilst retaining the underlying relationship between the attributes in terms of frequency or similarity, as mentioned above.

The conversion component either performs this dimension reduction automatically once the data record is accessed based purely on string pattern matching and similarities, or the user previously specifies which attributes are considered to relate to the same attribute and are hence variants of each other.

Preferably, and in particular for the interpretable variants of the data miner tools DMC, the arrangement 100 includes a graphic display generator GDG that is configured to generate on a display unit DU, a graphics display GD that includes a representation of the discovered pattern. In addition, or instead, the computed category operators may also be suitably displayed such as in list ranked according to their score.

Preferably the system includes a dynamic feedback loop in form of a user interface UI through which a user can provide input to influence the computation of the categorizer CAT and/or the data mining component DMC. The user can change any one of or combination of attribute values, the computed category operators, in particular a type thereof and other changes.

Preferably but not necessarily, the user interface is arranged as a graphical user interface GUI. To this end the, arrangement 100 includes a user interface generator UIG that is configured to produce a graphical user interface representation GUI of the user interface UI on the display unit DU or a different display unit. It is through this user interface GUI that the user can modify attributes and/or the computed category operators. Other user interactions are also envisaged herein. The user interaction as envisaged herein is dynamic in that the pattern and/or the category operators are re-computed by the miner DMC or the categorizer CAT, respectively, in direct response to the user inputting the changes. Preferably, the graphical user interface generator UIG and the graphics display generator GDG co-operate or are integrated to produce the graphic interface GUI to include the graphics display GD for representing the pattern and/or the category operators computed by categorizer CAT. The user interactions that are afforded by the user interface UI include, but are not limited to, adding or deleting attributes, changing attribute values or changing the type of the category operator. For instance, instead of a simple thresholding, the user may change the threshold into a single range or resolve the threshold or single range into multiple ranges.

Specifically, once a boundary value a or b of a category operator or the type of the category operator has been changed and/or once the user manipulates the attributes in the data set DS, the categorizer CAT is restarted to re-compute the category operators in response thereto. In addition, such a change also triggers a re-mining by the data mining component DMC, based on the new attributes and/or new category operators.

It will be understood from the above that changing the single bound in a threshold type operator or by changing both bounds in a range-type operator is essentially an act of overriding the values for the bound(s) previously computed by the CAT. If any of this is done, the categorization is not re-computed but it is only the pattern discoverer DMC that is rerun. However, in case of range type category operators, changing only one of the bounds will trigger a re-computation of the other, unchanged bound. Also, by merely changing the type in the threshold-type operator and leaving the single bound unchanged, this too will in general trigger a re-computation by categorizer CAT.

In the following FIGS. 2-4 we discuss and describe various embodiments of the graphics user interface GUI generatable by the user interface generator UIG. The graphical user interfaces are configured herein for graphical and interactive input through a pointer tool such as a mouse, stylus, through touch or gesture action in a touch screen. In such schemes, the graphical user interfaces are rendered as a collection of interactive widgets that allow invoking desired changes by selection of said widget commands through the pointer tool or touch/gesture to define events. In an event-driven frame-work, the events are handled by an event-handler to locate and invoke an appropriate routine or functionality from a library or similar. Although GUIs are preferred herein, this is not mandatory and non-graphical user interface UI variants such as text-based input schemes via keyboard or voice-based input via microphones and others are also envisaged in alternative embodiments and so are user input schemes based on a combination of such graphical and non-graphical input elements.

Figure 2:
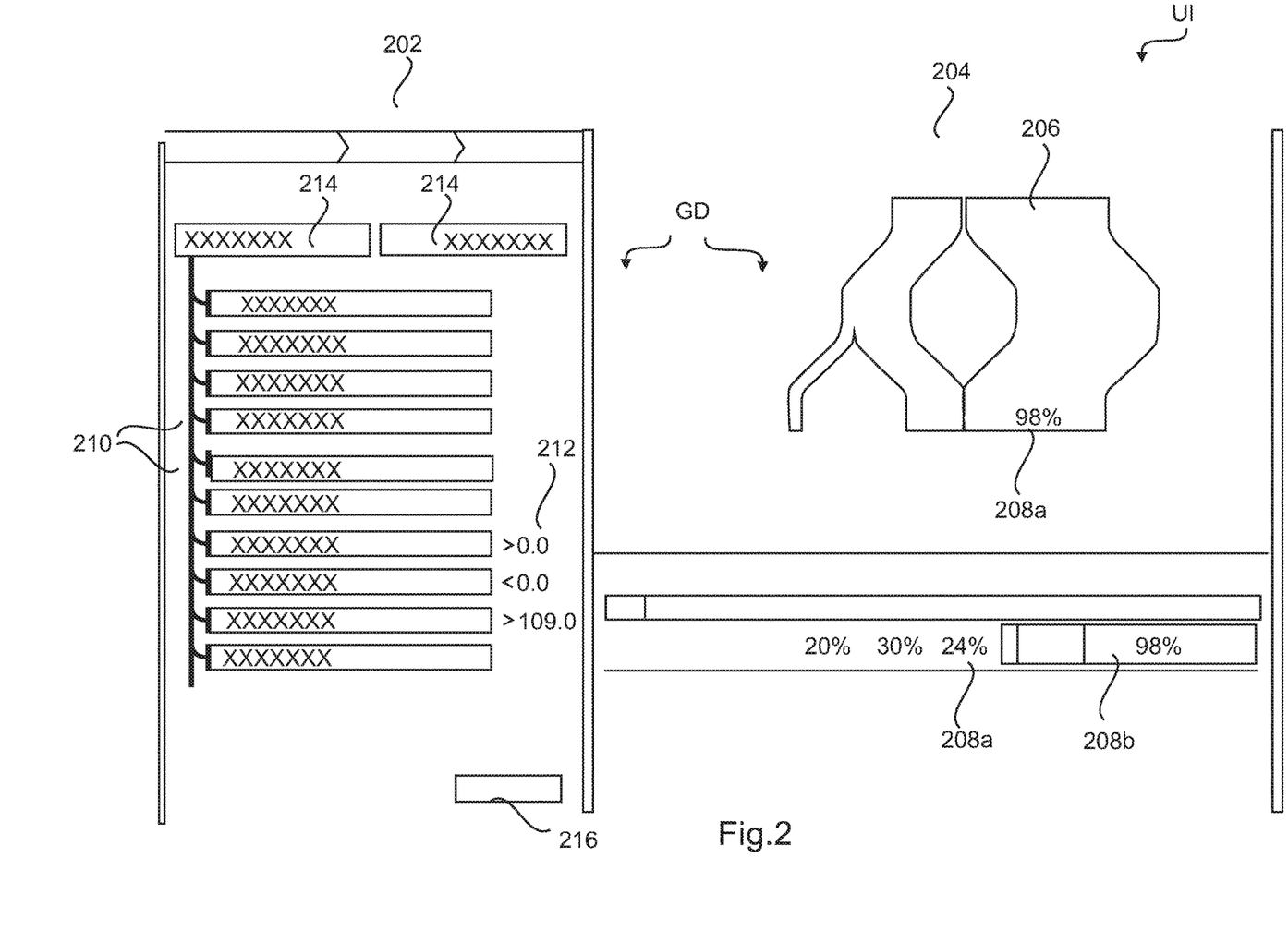
FIG. 2 shows a graphics display generated by the system in FIG. 1 according to one embodiment.

Turning now to FIG. 2, this is a schematic representation of a graphics display GD as generated by the graphics display generator and the user interface generator UIG. The graphics display includes two panes. One pane, shown on the left, is a categorization pane 202 that includes graphical representations 210 of the attributes, preferably displayed in association with their identifiers, all schematically shown as "XXXX", it being understood that these strings differ in general: PCI related entries may include: "HEART_RATE", "HEIGHT", "WEIGHT", "Radiation Dose", "Age", "No. of Ablations", "No. Drug Eluting Stents Used", "No. Stents Used", "Longest Stent/Treated segment", "Largest balloon/Stent Used", "No. In-stent restenosis attempted", "No. Lesions Successful", "No. Lesions Attempted", etc.

Preferably, there is also a representation of the target variable(s) 214 against which the data mining is to be performed.

The graphics display further includes, in association with the attributes 210, the associated category operators 212 as computed by the categorizer CAT. Preferably but not necessarily, the attributes are listed and ranked according the score incurred when computing the category operators in the score based optimization as explained earlier.

For instance, the attribute shown first in the list achieved the highest score whilst, the attributes under it achieved a lower score, etc. Graphic representations other than the list format that are suitable to represent the rankings to the user are also envisaged.

Optionally, there is an additional pane, the data mining tool 204, to display the data mining results as provided by mining tool DMC. Pane 204 includes, for instance, a graphical representation 206 of the data mining outcome. The exemplary representation shown in FIG. 2 is a waterfall diagram with cascades whose respective widths represent the respective size of the category operators in percentages. Statistical descriptions such as "false positives", "f-measure", p-value are shown in information sub-panes 208a-c. Widgets for the respective attributes 201 and in particular for those for the category operators 212 are interactive so that the user can change attribute-values and/or a type of same by point tool action (e.g. mouse-click) or by finger/gesture/touch screen action. Selecting the widget of a certain attribute allows accessing a list of the associated attributes with editing options such as change, delete or add values, etc. New attributes that emerged later, e.g. from other database queries, may be added to complete the base data.

Figure 3:
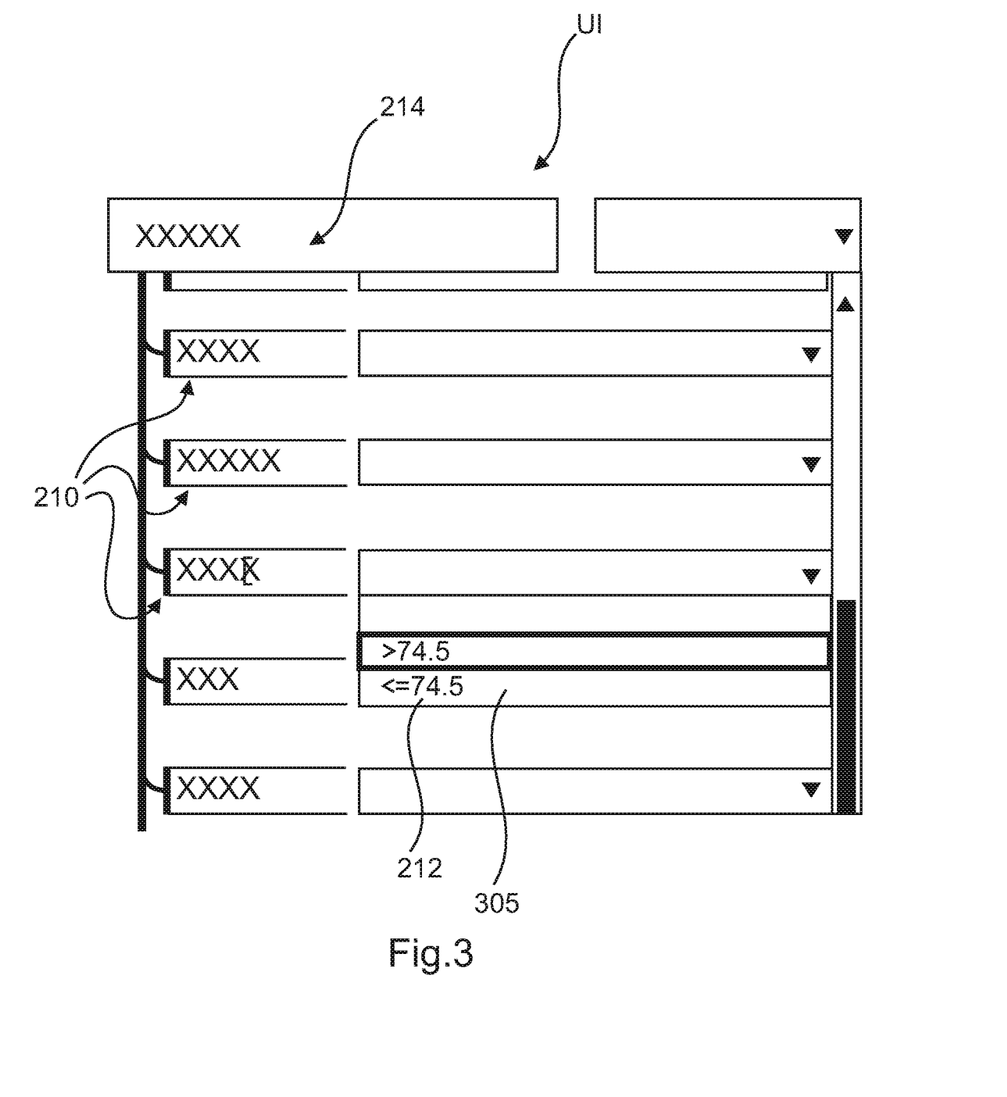
FIG. 3 shows another embodiment of a graphics display for a graphical user interface.

The close-up in FIG. 3 shows a more detailed view of the mentioned category operator changing functionality. In this embodiment, upon clicking with a pointer tool or by touch screen or gesture action on the respective tab for the attribute 210, the user invokes a widget 305 which shows the current category operator and different alternative type(s) thereof. In one embodiment, this type selector widget 305 is arranged as a drop-down menu, but alternative embodiments are also envisaged. In the exemplary embodiment shown, category operator for attribute "AGE" ("larger than 74.5") is currently active. The user can flip and change this type into the logical complement category operator type, which in this case results in the category operator "less than or equal to 74.5". If this is done, an event handler (not shown) recognizes that the user requested a change of the type of the category operator and this is then propagated to the categorizer who re-runs the computation based on the new selected category operator type. As a result of this a change in category operators is most likely to result in a change of the computed pattern which is likewise updated by tool DMC and updated representation shown 206 is displayed in the data mining pane 204 of FIG. 2. A similar interactive editing functionality can be provided to change edit the attribute values themselves as mentioned above in relation to FIG. 2.

Figure 4:
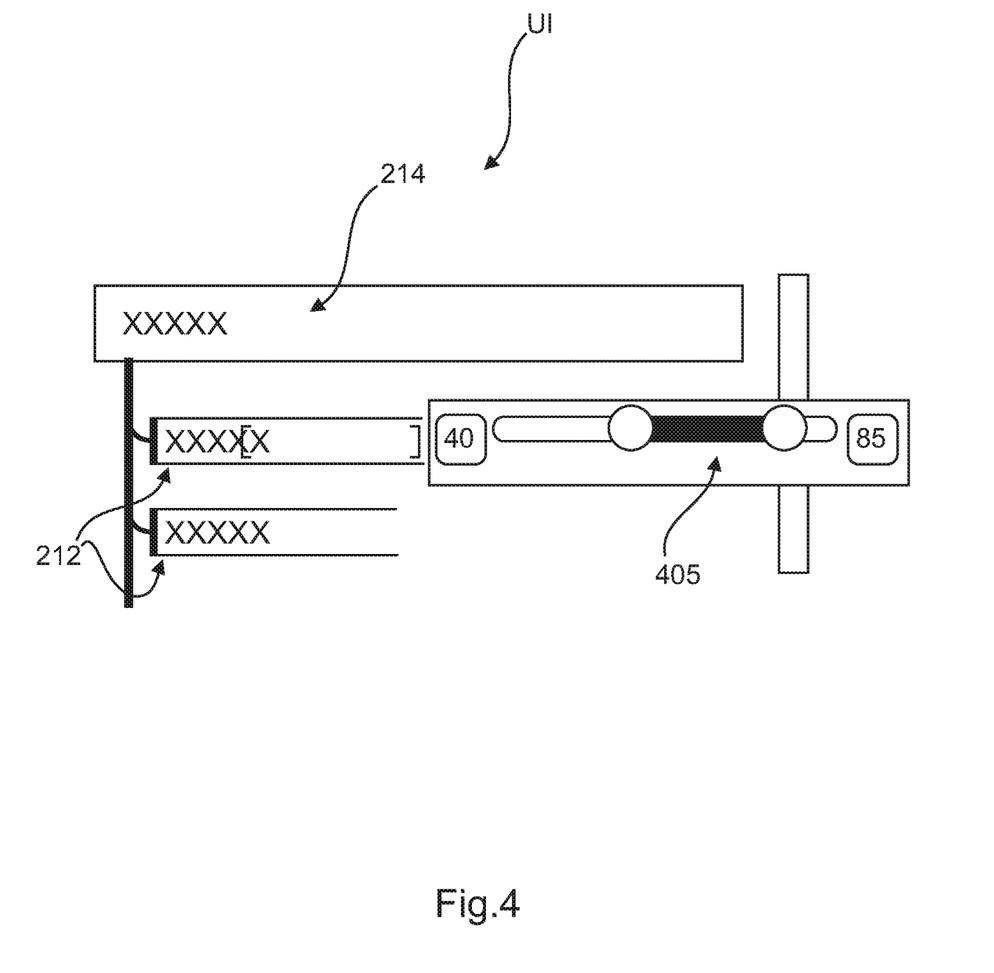
FIG. 4 shows a graphic display according to another embodiment for a graphical user interface.

FIG. 4 is yet another embodiment of a graphical user interface widget that allows the user to change a range-type category operator. Specifically, and in this embodiment, the bounds can be changed to essentially override the bounds computed by the categorizer CAT in order to let the user incorporate domain knowledge. In one embodiment, a bound manipulator widget 405 is provided as a double-sided sliding tool as exemplary shown in this figure. Bound manipulator 405 lets the user change the range bounds of the category operator by sliding the left and right boundary widgets (shown as circles) which are virtually slidable along a virtual bar element. Currently, and as shown by way of example in the figure, the lower bound for attribute "AGE" is set to 40 whilst the upper bound is 85. By sliding respective widgets for these bounds, one or both of these can be changed. Once the change is so requested, suitable signal is issued and intercepted by an events handler to effect that the data mining computation by DMC and the associate rendering in pane mining pane 204, in particular the statistics 208a-c and the diagram 206, are accordingly updated. In addition, and as explained above in relation to FIG. 3, a type selector 305 may be provided to let the user not only change the bound(s), but also the type by toggling between open, closed and the two open-closed interval definitions, e.g. "[*, *]->[*, *)->(*, *]->(*, *)", this particular sequence being merely exemplary with others being likewise envisaged herein. If only one of the bounds (upper or lower) is changed, whilst the other remains unchanged, this one-sided bound change request will trigger a re-computation of the categorizer of the unchanged bound. In a threshold/dichotomy type operator, change of the type from > or < to their respective logical complements =<, => may trigger a re-computation by categorizer CAT whilst changing the bound value a is an override operation which in general will not trigger the categorizer CAT to re-compute the category operator. In this later case, only the data miner component may be triggered to re-mine for the pattern.

In all of the above embodiments FIG. 2-4, in order to help the user track the changes, a suitable indicator may indicate to the user whether or not this attribute has been changed, e.g., by displaying the note or tool tip "not edited". The GUI may further include a "revert" button to revert to the original data and settings.

In all the above, changes of attributes or category operators will automatically trigger a re-computation and re-rendering to update the GUI, preferably in quasi-real time to allow the user to quickly mine the data DS for the pattern. Specifically, in any one of the above GUI embodiments FIG. 2-4, if the user requests a change of type or bound, and the categorizer CAT re-computes said bound or type, the first K (≥2) best results may be shown to the user rather than a single result that came out top in the metric driven optimization. The K (≥2) best results may be shown for instance in list form in a superposed drop-down menu widget. The user can then select or re-select from the list and observe and explore and experiment how the associated data mining result changes for different selections from the list. But this is not to exclude the alternative embodiment, where it is only the single best categorization result (bound or type) that is displayed.

It should be noted that in the above, the various components of the arrangements 100 are connected by wired or wireless connection in a suitable communication network. For instance, a cloud based architecture for the arrangement 100 may be envisaged where the categorizer CIT resides in one server whilst the data mining component DMC is run by a different, remotely located server. Preferably, the graphical user generator is run at the user's end terminal such as on a desktop computer, laptop, personal digital assistant (PDA), a tablet, smartphone or other. In another embodiment the components CAT and DMC and UIG run on a user's computer, whilst the data base management system DB is situated remotely at a central server or itself is distributed across a number of different data bases from which the data can been collected. A manifold of other architectures is also envisaged herein including one where all of the components run centrally on a single server.

In the alternative, or in addition, some or all components of the arrangement 100 may be arranged in hardware such as a suitably programmed FPGA (field-programmable-gate-array) or as hardwired IC chip.

Figure 5:
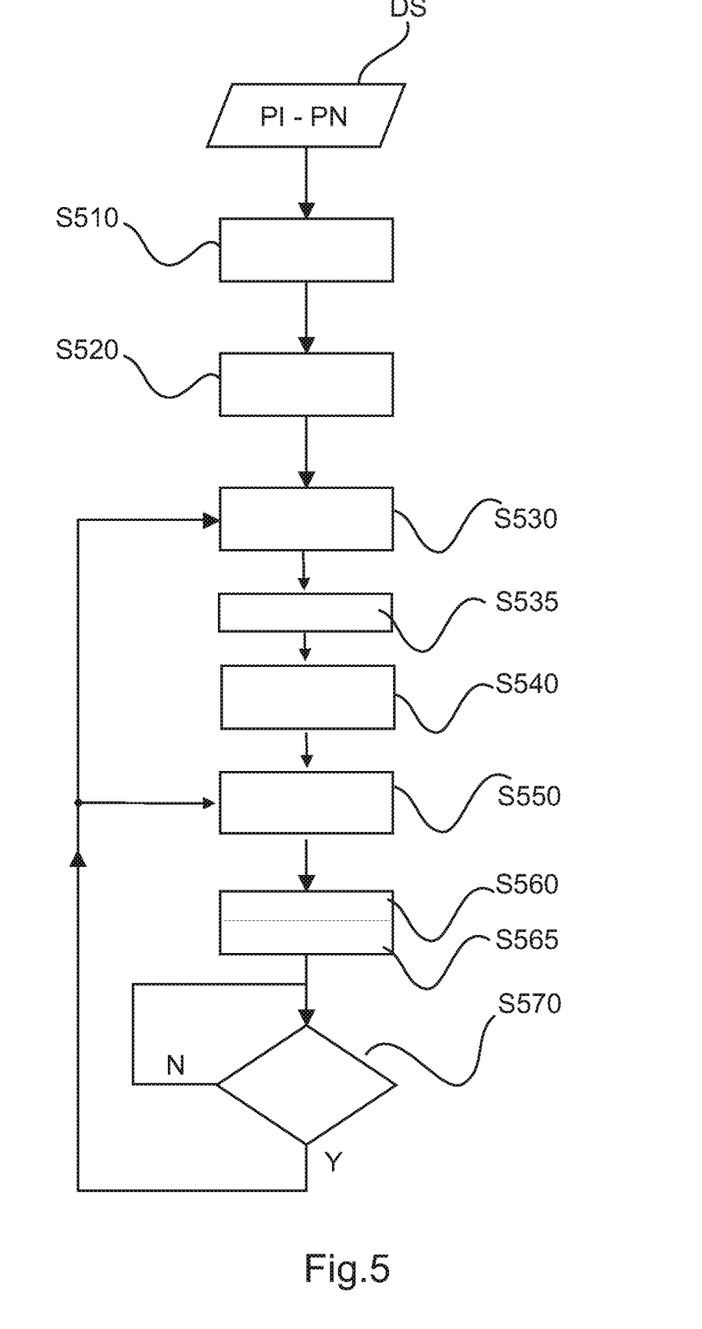
FIG. 5 shows a flow chart of a method of data processing.

Reference is now made to FIG. 5 which shows a flow chart for a data processing method to provide further details on the operation of the data processing system in FIG. 1. It will be understood however, that the flow chart may also be read in its own right and is not necessarily tied to the architecture as shown in FIGS. 1-4.

At step S510 data is received from a storage. The data is preferably structured. The data may include in particular at least one data record with attributes. At least one attribute has at least one missing value in at least one of the records.

At step S520 which is optional, a plurality of attribute strings that relate to the same attribute, are reduced and consolidated into a single one.

At step S530 the data is categorized by computing category operators. In one embodiment, when computing the category operators, any data record with at least one missing value for an attribute of interest is not included in the computation. In particular, the record with the missing value is ignored when computing a category operator for the specific attribute where the missing value occurs. Specifically, a data record may be ignored when computing the category operator for a certain attribute but then may not be ignored when computing a category operator for another-attribute where there is no longer a missing value, that is, where a value is present. The computing of the category operators for the different attributes is based on a user or otherwise pre-specified type for the category operators.

For instance, in one embodiment, the user specifies for each attribute of interest whether the category operator type to be computed is a threshold (dichotomization) type or whether it is a two-sided interval. The categorization may also be based on a multiple of such disjoint intervals. Preferably, the computation of the categorization operators is based on specifying a target variable as mentioned above in relation to FIG. 1. The target is to be used later for data mining of the data based on the categorization operators. The computation of the category operators is furthermore based on a score that represents an optimization criterion for computing the category operators.

According to one embodiment, the score is computed as the information theoretic quantity of information gain. As mentioned above, other scores are also envisaged, such as Gini Index, Kullback-Leibler divergence and others. Preferably the scores computed may also be used to rank the category operators across the attributes.

Computation of a category operator at step S530 will now be explained in more detail with respect to the information gain score, but this exemplary and other scores may be used instead, as mentioned above. It will be understood that the selection of a target is preferred and the computation of the score is tailored to that target. The target may be one of the attributes in the data but is not necessarily so, as long as it can be established whether or not the target variable applies to the individual records or not.

It will be appreciated, that the skipping of data records with missing values can be implemented by running a pattern string matcher across the different data records per attribute to so find and eliminate records with missing records. The identification of the missing values may be done up front for the whole data set but preferably is included or "interleaved" with the computation of the category operators. Broadly, an optimization algorithm is run, that attempts to find a category operator by optimizing (e.g. maximizing) the score. Different optimization algorithms (maximizer or minimizers), such as conjugated gradients etc. can be used. As explained earlier, the score may be formulated as an objective function, in dependence on the bounds of category operators sought and, preferably, the target. If the optimization problem is formulated as a minimization, the objective function is more aptly called a "cost".

Alternatively, the algorithm may be a search algorithm, such as a greedy type search algorithm, where, at given increments, the algorithm loops through possible values of the bound(s) of the category operators whilst computing the respective score. A list of category operators with the respective score is then formed and re-sorted during the looping so that the best score (e.g., highest score) appears first or last, as the case may be. At the conclusion of the iterations, the best category operator relative to the given score can then be read out from the last or first entry of the list. It will be appreciated that the above may be reformulated with a different objective function as one of minimizing a cost rather than maximizing a score.

The information gain as a specific embodiment for the category operator score may be formulated as follows: Information gain is employed herein as an informative/predictive measure for a target specific numeric categorization in our exemplary embodiment. For (categorical) target attribute t with the following non-missing distinct value (level) set $\{t_c\}$, we can calculate the level distribution $d_0=\{p_c\}$ where $p_c$ is the probability of level $t_c$. $p_c$ can be computed as the fractions of all domain elements that satisfy the target attribute tc. Its information (relative entropy) can be calculated as:

$$I(d_0) = \sum_c p_c \log p_c \quad (3)$$

For a numeric attribute m, after a categorization of any type, all data records are separated into two sets: one "within range" (or <=) and its complement, that is, "out of range" (or >), where records with missing values in m or t are skipped for seamless "on-the-fly" handling. A data cleansing operation that would interrupt the downstream data mining can be so avoided. Assume that the two sets have counts $n_1$ and $n_2$ respectively, and the two sets of records correspond to target level distributions $d_1=\{p_{c1}\}$ and $d_2=\{p_{c2}\}$ where $p_{c1}$ and $p_{c2}$ represent the probabilities of the target attribute t in the two sets, respectively. The new information is then:

$$I(d_1, d_2) = n_1/(n_1+n_2)\sum_{c1} p_{c1}\log p_{c1} + n_2/(n_1+n_2)\sum_{c2} p_{c2}\log p_{c2} \quad (4)$$

And so the information gain I is:

$$I=I(d_1,d_2)-I(d_0) \quad (5)$$

I is non-negative and the larger I is, the more "informative" the numeric categorization is for the target attribute t. Other, scores or metrics such as "mutual information" based that are equivalent to I as per (5) above and/or that modulate with an entropy-based quantification of information are also included and envisaged herein.

The following pseudocode snippet provides an embodiment of a dichotomization numeric categorization for a selected target attribute t:

```
Obtain target attribute t's distinct values {t_c}
Get target level distribution d_0 of {t_c} of t's non-missing records
For each numeric attribute m_i in data
{
    maxI_i ← 0; index_i ← 0
    Order m_i's non-missing distinct values into a list: {v_j}
    For each v_j in {v_j}
    {
Get target level distribution d_1 of {t_c} on records <= v_j, skipping missing values       (6)
Get target level distribution d_2 of {t_c} on records > v_j, skipping missing values        (7)
        Calculate informative measure (information gain) I_j using d_0, d_1, d2
        If (I_j > maxI_i)
        {
            maxI_i ← I_j, index_i ← j
        }
    }
    Transform m_i record numeric values into categories "<= v_{indexi}" and ">
v_{indexi}" accordingly                                                                      (8)
}
Output all transformed m_i attributes
A single range categorization (eg, [a, b] and similar) can be implemented by
the following pseudocode:
    Obtain target attribute t's distinct values {t_c}
    Get target level distribution d_0 of {t_c} of t's non-missing records
    For each numeric attribute m_i in data
    {
        maxI_i ← 0; index_set_i ← {0, 0}
        Order m_i's non-missing distinct values into a list: {v_j}
        For each v_j, v_k in {v_j}, where v_j <= v_k
        {
Get count distribution d1 of {t_c} on records [vj, v_k], skipping missing values            (9)
Get count distribution d2 of {t_c} on records not in [vj, v_k], skipping missing values     (10)
        Calculate informative measure (information gain) I_{jk} using d_0, d_1, d2
        If (I_j > maxI_i)
        {
            maxI_i, ← I_{jk}, index_set_i ← {j, k}
        }
    }
    Transform m_i record numeric values into categories "[v_{index_set_i[0]},
v_{index_set_i[1]}]" and "others" accordingly                                                (11)
}
Output all transformed m_i attributes
```

Each pseudo code includes nested looping structures to loop at suitable increments over attribute values and to ensure that the information measure I is non-decreasing. In this manner a greedy search style of the best bound $v_i$ or bounds ($v_i$, $v_j$ is found. In the above pseudocode I can be replaced by any other suitable score functions, and by reversing the looping and comparators, a search minimizing a cost function (instead of maximizing the score I) may be implemented instead. The single range pseudocode may readily extended by another loop to cover multiple ranges, if required.

As can be seen in lines (6), (7), (9), (10) of the pseudocode, the skipping of the missing values is done whilst the computation of the category operators are ongoing ("on-the-fly") to increase responsiveness. The specific loop structure is merely one embodiment however, and the on-the-fly record skipping for missing values can be done by another suitable construction.

In lines (8) and (11), the computed category operators are applied to the data set $m_i$ to obtain the categorized data: for instance, suppose we have data: $m_i$=[0.5, 0.6, ?, 1.3, 2.3, ?, 0.4, . . . ]. Further suppose the computed operator is a threshold CO="<1". The column is then transformable into categorized data: $CO(m_i)$=[<1.0, <1.0, ?, >=1.0, >= 1.0, ?, <1.0, . . . ], with "?" indicating missing values.

As can be further seen in the pseudocode snippets, the count or probability distribution $d_0$ is function of the target t and $d_0$ is a function of the metric I. In other words, the metric I is a function of the target t. Configuring the metric as a function of the target t allows securing more tailored results for the data-mining task. Of course the specific functional relationship between the metric I and the target t may differ from embodiment to embodiment any may not necessarily take the specific functional form as shown in the pseudocode snippets. Having said that, configuring, as has been done above, the metric I as a function of the target level distribution (or functional reformulations thereof) has proved useful in a wide range of applications.

In all of the above embodiments of the categorization step S530, the optimization is run over the bounds a or a, b to find the best category operator for a given type. In an extension of the above disclosure, an enlarged variable set may be used, where the optimization is run not only over the bound but also over the type. This can be implemented in the pseudocodes above by including further loops over the category operator types.

The use of the information gain measure in step S530 is different from its use in decision tree learning algorithms. In decision tree algorithms there is an iterative splitting on multiple nodes, conditioned on earlier splittings in previous nodes whilst for present purpose there is no conditioning on previous nodes.

The computed category operators may then be applied to the data DS to categorize or transform the attributes in the data set DS to form categorized data.

Using the proposed categorization S530 with interpretable data mining tools DMTC such as described in Applicant's WO2017072010A1 or WO2017072628A1, it has been observed in experiments that the predictive power can be increased by 21% and the odds-ratio by about 50%.

At an optional step S535, if more than one category operator is so computed, these may be ranked according to cost or score.

Preferably it is the best (relative to the used score) category operator for each attribute that is output at step S540. However, in alternative embodiments, it is the best K≥2 category operators per attribute that are output and the user selects the one they see fit. The K best operators may be displayed, for instance, in a drop-down interface for convenient selection by the user as mentioned above in relation to the GUI embodiments in FIGS. 2-4.

At step S550, data mining algorithm is used to compute a pattern based on the category operators, in particular, in the categorized data. In one embodiment a decision tree type algorithm is used but other variants such as neural networks, support vector machines and others are also envisaged herein. In short, any algorithm is envisaged that requires a categorized data or that works better with categorized data. In the alternative or in addition, graphics driven, "semi-automatic" data mining tools of the interpretable type are used, in which the proposed method can be practiced with particular benefit. Exemplary embodiments of interpretable data miner tools have been described earlier by Applicant at WO2016030436A1 and WO2017072010A1 and WO2017072628A1, all incorporated herein.

At step S560 a representation of the data mined pattern and/or the data categorized by the categorization operators is/are displayed either individually or alongside each other.

Optionally, a user interface if provided in step S565, preferably graphical, and displayed, for the user to change the initial data, in particular to manipulate attributes therein and/or to change computed category operators, e.g. the bound(s) and/or the type.

If a request for a user to change the data and/or attributes is detected at step S570, a request is made to re-compute the categorization and/or the data mining now based on the updated information as requested by the user.

When user chooses to change a range value (either lower or upper bound of a candidate range as computed earlier in the categorizer step S530), the system may recommend the top K values for the unchanged bound to be chosen. This can be realized by a variation of the above pseudocode for range categorization. For example, for the case of lower bound recommendations, it means $v_k$ is fixed by user, and all $v_j <=_v k$ are looped over, and K of them are output according to the top K ranked informative measures (eg, information gain) rather than finding only one best $v_j$. Similarly, for the case of upper bound recommendations, this translates into a task of finding the top K $v_k$ with $v_j$ fixed by the user.

Referring back to the attribute reduction step at step S520, in noisy data, even categorical attributes can have excessively many levels, e.g. due to manual input variations in healthcare systems. To handle this challenge uniformly with purely numeric values, an encoding scheme can be selected to convert variants of string values of the same attributes, to numeric values which reflect their original relationship. For example, assume the following data:

Input, Target:
[Diabetes, Y] x 40 times
[Diabetes, N] x 10 times
...
[DM, Y] x 30 time
[DM, N] x 10 times
...

-continued

[variant 3, Y] x 2 times
[variant 3, N] x 2 times
...
[variant 200, Y] x 0 time
[variant 200, N] x 1 time As can be seen in the above exemplary data, the column has 200 distinct variants: "Diabetes", "DM", "variant 3", ..., "variant 200", with respective frequencies, which can be ranked thus: 50, 40, 4, ..., 1. Applying what is proposed herein, one can encode the non-numeric values into numeric values to retain their original relationship as per the frequency ranking: Diabetes->1, DM->2, variant 3->3, ... variant 200->200.

The values are now numeric, and the categorization step S530 can be applied to the so encoded data. Assuming for instance, that the categorization step S530 is 2 (>=, <), then all these values would be categorized, and the categorized values would be "Diabetes", "DM", and all others (for the remaining variants). In other words, a reduction of dimension has been achieved.

In one embodiment, the reduction step S520 can be based on similarity measures of strings. In another embodiment, pair-wise local or global alignment can be applied to all level pairs to calculate edit distances. With the edit distances calculated, hierarchical clustering based on average linkage can be applied, where each level has distances calculated against both, individual levels and level groups ("clusters"). These distances then can be converted to numbers by setting a reference value.

In yet another embodiment, Huffman coding can be applied to sort out the distances among the levels, and similarly the distances can be converted to numbers by setting a reference value.

In yet another embodiment, knowledge-based encoding schemes can be provided. Users can pre-define a concise set of major levels of interest, optionally with their distance measures and thresholds. Then all variant levels are compared to the concise set with the distances calculated. All variant levels are then converted into numeric values which can be handled by the auto-numeric categorization described above. Once the number of attributes has been reduced as per step S520, the categorization can then proceed as explained above.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A data processing system, comprising:
   an input interface configured to receive data to be data-mined for a pattern given a target, the data comprising at least one record with at least one missing value;
   a categorizer configured to compute a plurality of category operators suitable to categorize said data, wherein the computing by the categorizer of the plurality of category operators includes computing respective metrics that are functions of parameters of the plurality of category operators, and the categorizer ignores the at least one record when computing at least one of the plurality of category operators, and the computing of the plurality of category operators to categorize said data is interleaved by checking a respective record of said data for missing values; and
   a graphics display generator configured to render, on a display unit, a graphics display that includes a representative of the plurality of category operators, and visually modulate, in the graphics display, relationships between the plurality of category operators and their respective sizes, wherein each category operator is ranked respectively according to their best metric.

2. The data processing system of claim 1, wherein the computed metric includes either information gain or Kullback-Leibler divergence.

3. The data processing system of any claim 1, further comprising:
   a data-mining component (DMC) configured to mine, or help a user to mine, the data categorized by the plurality of category operators, for the pattern.

4. The data processing system of claim 1, further comprising:
   a user interface that is configured to allow a user to change the data and the plurality of computed category operators, wherein, in response to said change, the categorizer is further configured to recompute the plurality of category operators.

5. The data processing system of claim 1, further comprising:
   a conversion component configured to reduce a plurality of string values in the data into numeric values according to either their frequency or similarity, before the categorizer computes the plurality of category operators.

6. The data processing system of claim 1, wherein the graphics display generator is further configured to render, on the display unit, a graphical representation of the data mining results provided by a data mining tool.

7. The data processing system of claim 6, wherein the graphical representation is a waterfall diagram, wherein respective widths of cascades represent respective sizes of category operators.

8. A method of data processing comprising:
   receiving, by an input interface, data to be data-mined for a target, the data comprising at least one record with at least one missing value;
   computing, by a categorizer, a plurality of category operators suitable to categorize said data, wherein the computing of the plurality of category operators includes computing respective metrics that are functions of parameters of the plurality of category operators, and the categorizer ignores the at least one record when computing at least one of the plurality of category operators, and the computing of the plurality of category operators to categorize said data is interleaved by checking a respective record of said data for missing values; and
   rendering, by a graphics display generator, on a display unit, a graphics display that includes a representative of the plurality of category operators, and visually modulate, in the graphics display, relationships between the plurality of category operators and their respective sizes, wherein each category operator is ranked respectively according to their best metric.

9. A non-transitory computer readable medium having stored thereon instructions executable by a data processor to carry out a method of intelligent numeric categorization of noisy data, the non-transitory computer readable medium comprising:
- instructions for receiving, by an input interface, data to be data-mined for a target, the data comprising at least one record with at least one missing value;
- instructions for computing, by a categorizer, a plurality of category operators suitable to categorize said data, wherein the computing includes computing respective metrics that are functions of parameters of the plurality of category operators and ignores the at least one record when computing at least one of the plurality of category operators, and the computing of the plurality of category operators to categorize said data is interleaved by checking a respective record of said data for missing values; and
- instructions for rendering, by a graphics display generator, on a display unit, a graphics display that includes a representative of the plurality of category operators, and visually modulate, in the graphics display, relationships between the plurality of category operators and their respective sizes, wherein each category operator is ranked respectively according to their best metric.

* * * * *